(12) United States Patent
Kagaya

(10) Patent No.: US 10,299,666 B2
(45) Date of Patent: May 28, 2019

(54) ENDOSCOPE SYSTEM

(71) Applicant: FUJIFILM Corporation, Tokyo (JP)

(72) Inventor: Makoto Kagaya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 631 days.

(21) Appl. No.: 13/949,474

(22) Filed: Jul. 24, 2013

(65) Prior Publication Data
US 2014/0031623 A1 Jan. 30, 2014

(30) Foreign Application Priority Data

Jul. 25, 2012 (JP) ................................. 2012-164881

(51) Int. Cl.
*A61B 1/00* (2006.01)
*A61B 1/06* (2006.01)

(52) U.S. Cl.
CPC ............ *A61B 1/06* (2013.01); *A61B 1/00009* (2013.01); *A61B 1/0638* (2013.01); *A61B 1/0653* (2013.01)

(58) Field of Classification Search
CPC ............ A61B 1/00006; A61B 1/00009; A61B 1/0638; A61B 1/0653; A61B 1/063; A61B 1/06; A61B 1/043
USPC .................................................. 600/180, 178
See application file for complete search history.

(56) References Cited

U.S. PATENT DOCUMENTS

| | | | | |
|---|---|---|---|---|
| 8,858,429 B2* | 10/2014 | Mizuyoshi | ............ | A61B 1/0653 600/118 |
| 8,936,548 B2* | 1/2015 | Ozawa | ................. | A61B 1/0638 600/178 |
| 8,970,685 B2* | 3/2015 | Minetoma | .......... | A61B 1/00009 348/65 |
| 9,125,274 B1* | 9/2015 | Brunault | ............ | H05B 37/0281 |
| 2002/0177751 A1* | 11/2002 | Ueno | ................. | A61B 1/00009 600/160 |
| 2002/0179815 A1* | 12/2002 | Forke | ................. | H05B 41/3922 250/205 |

(Continued)

FOREIGN PATENT DOCUMENTS

JP 2004-24611 A 1/2004
JP 2006-341077 A 12/2006
(Continued)

OTHER PUBLICATIONS

Japanese Office Action dated Jun. 16, 2014, issued in corresponding Japanese Patent Application No. 2012-164881.

*Primary Examiner* — Timothy J Neal
*Assistant Examiner* — Jae Woo
(74) *Attorney, Agent, or Firm* — Birch, Stewart, Kolasch & Birch, LLP

(57) ABSTRACT

An endoscope system is provided by which observation image brightness can be suppressed from irregularly fluctuating before and after changing of an observation mode and observer's discomfort feeling can be reduced. The endoscope system includes an imaging element, an image processing section that generates an observation image from an imaging signal, a display section that displays the observation image, an illumination mode changing section that changes illumination modes of a light source device, an image processing mode changing section that changes an image processing mode, and a light source control section that controls the light source device.

20 Claims, 12 Drawing Sheets

(56) References Cited

U.S. PATENT DOCUMENTS

| | | | |
|---|---|---|---|
| 2002/0195576 A1* | 12/2002 | Inoue | G01V 8/12 250/559.29 |
| 2003/0146919 A1* | 8/2003 | Kawashima | G09G 3/3406 345/609 |
| 2004/0037454 A1 | 2/2004 | Ozawa et al. | |
| 2004/0155976 A1* | 8/2004 | Suda | G03B 13/36 348/345 |
| 2006/0279710 A1* | 12/2006 | Tani | H04N 5/7458 353/85 |
| 2007/0055106 A1* | 3/2007 | Moriyama | A61B 1/00096 600/178 |
| 2008/0194972 A1* | 8/2008 | Gono | A61B 1/0005 600/476 |
| 2009/0058999 A1* | 3/2009 | Gono | A61B 1/00009 348/71 |
| 2009/0065679 A1* | 3/2009 | Tanimoto | H04N 5/33 250/208.1 |
| 2010/0123775 A1* | 5/2010 | Shibasaki | A61B 1/00009 348/68 |
| 2011/0034770 A1* | 2/2011 | Endo | A61B 1/0638 600/118 |
| 2011/0071352 A1* | 3/2011 | Ozawa | A61B 1/0638 600/109 |
| 2011/0071353 A1* | 3/2011 | Ozawa | A61B 1/0638 600/109 |
| 2011/0237894 A1* | 9/2011 | Ozawa | A61B 1/043 600/168 |
| 2012/0075449 A1* | 3/2012 | Yasuda | A61B 1/00009 348/68 |
| 2012/0078044 A1* | 3/2012 | Yamaguchi | A61B 1/045 600/109 |
| 2012/0116159 A1 | 5/2012 | Mizuyoshi et al. | |
| 2012/0147166 A1* | 6/2012 | Minetoma | A61B 1/00009 348/68 |
| 2012/0148277 A1* | 6/2012 | Takezawa | G03G 15/04054 399/51 |
| 2012/0220824 A1* | 8/2012 | Kaku | A61B 1/00009 600/109 |
| 2013/0321602 A1* | 12/2013 | Hayama | A61B 1/00009 348/68 |
| 2014/0031623 A1* | 1/2014 | Kagaya | A61B 1/00009 600/109 |
| 2014/0161369 A1* | 6/2014 | Ishihara | A61B 1/043 382/274 |

FOREIGN PATENT DOCUMENTS

| | | |
|---|---|---|
| JP | 2009-148487 A | 7/2009 |
| JP | 2011-10998 A | 1/2011 |
| JP | 2012-160 A | 1/2012 |
| JP | 2012-29703 A | 2/2012 |
| JP | 2012-50641 A | 3/2012 |

* cited by examiner

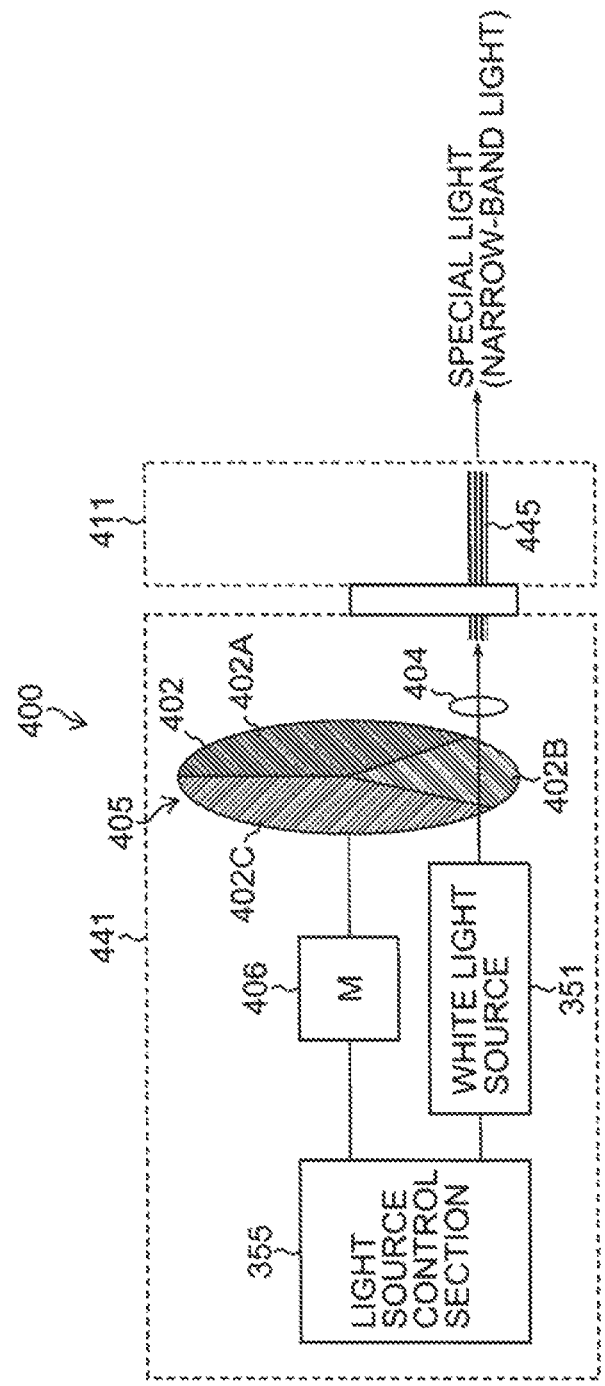

ENDOSCOPE SYSTEM

BACKGROUND OF THE INVENTION

Field of the Invention

The present invention relates to an endoscope system and specifically relates to an endoscope system capable of performing a normal (white light) observation using white light and a special light observation using special light.

Description of the Related Art

An endoscope system is used in recent years which applies specific narrow wavelength-band light (special light) to biological mucosa tissue to obtain tissue information at a desired depth of body tissue, or which can perform so-called a special light observation.

Using the special light observation, it is possible to visualize body information such, for example, as microstructure of a new blood vessel generated in a mucosa layer or a submucosa layer and enhancement of a lesion part, which information is difficult to obtain in a normal observation.

Upon changing of the observation mode from a normal observation mode of performing the normal observation to a special light observation mode of performing the special light observation, illumination light is changed from white light to special light, and image processing of generating an observation image which is to be displayed on a monitor apparatus from an imaging signal acquired by an imaging sensor is changed from image processing suitable for the normal observation mode to image processing suitable for the special light observation mode.

In the special light observation mode, since narrow-band light limited to a specific narrow wavelength region is used, there can be a case where sufficient light amount is not obtained. In such a case, deterioration of image quality of the observation image caused by shortage of the illumination light amount (darker observation image in the special light observation mode relative to the observation image in the normal observation mode) is concerned.

Japanese Patent Application Laid-Open No. 2011-010998 (hereinafter referred to as Patent Literature 1) discloses, in an endoscope apparatus including a blue laser light source and a violet laser light source, control of the light sources of calculating brightness information from an imaging signal obtained from an imaging element and increasing or decreasing an emitting light amount of each light source such that the image signal is at a desired brightness level.

Japanese Patent Application Laid-Open No. 2009-148487 (hereinafter referred to as Patent Literature 2) discloses, for an endoscope apparatus including a light source section that changes illumination light wavelength bands by switching filters and performing light amount control of holding brightness of an image displayed on a monitor constant, a technology of preventing large disorder in the monitor image in switching of an observation mode and enhancing response of switching of the observation mode by fixing the emitted light amount to the value immediately before switching in switching of the observation mode (in switching of the filters) and suspending the light amount control.

Japanese Patent Application Laid-Open No. 2012-050641 (hereinafter referred to as Patent Literature 3) discloses an endoscope system of controlling switching timing from image processing for a normal observation to image processing for a special light observation according to chronological response characteristics of a light source for the special light observation in switching from a normal observation mode to a special light observation mode.

Japanese Patent Application Laid-Open No. 2012-029703 (hereinafter referred to as Patent Literature 4) discloses an endoscope apparatus configured capable of continuously controlling each of emitted light amounts of narrow-band light and white light independently and configured to apply both of the white light and the narrow-band light at an arbitrary emitted light amount ratio for imaging and to set an object to be observed with narrow-band light (superficial vessels, gland ducts and the like) in the obtained observation image at the most suitable brightness level such that brightness values do not saturate over the whole observation image.

Japanese Patent Application Laid-Open No. 2004-024611 (hereinafter referred to as Patent Literature 5) discloses, for a fluorescent observation image processing apparatus including a fluorescent image mode and a normal image mode, image processing of performing signal processing corresponding to each mode.

SUMMARY OF THE INVENTION

However, when fluctuation (flickering) of brightness of the observation image projected on the monitor apparatus arises before and after changing of the observation mode, it is concerned that the observer suffers from discomfort feeling. In particular, when the observation image after changing of the observation mode becomes brighter relative to the one before changing, fluctuation of brightness of the observation image is subjected to enhancement.

Although the endoscope apparatus described in Patent Literature 1 optimizes the brightness level of the image signal of the observation image for each observation mode, there is no measure against fluctuation of brightness of the observation image in switching of the observation mode.

Although the endoscope apparatus described in Patent Literature 2 fixes the light amount value immediately before switching of the observation mode, since the real illumination light amounts are different from each other for individual kinds of light sources (illumination modes), brightness of the observation image discontinuously changes before and after switching of the observation mode, this causing flickering of the observation image. Furthermore, there is still a problem that the light amount control converges late albeit good response of the light amount control after switching.

Since the endoscope system described in Patent Literature 3 switches the image processing for the special light observation after the special light is stabilized when the normal observation mode is switched to the special light observation mode, after switching of the image processing, the observation image suitable for the special light observation can be obtained. Nevertheless, it is difficult to prevent fluctuation of brightness of the observation image until the special light is stabilized after switching of the observation mode.

Although the endoscope apparatus described in Patent Literature 4 optimizes brightness of the observation image as a whole, it cannot handle fluctuation of brightness of the observation image in switching of the observation mode.

The fluorescent observation image processing apparatus described in Patent Literature 5 also does not include a configuration for prevent fluctuation of brightness of the observation image in switching of the observation mode.

The present invention is devised in view of the aforementioned circumstances and the object aims to provide an endoscope system capable of preventing irregular fluctuation of brightness of an observation image before and after changing of an observation mode and reducing discomfort feeling of the observer.

In order to achieve the above-mentioned object, an endoscope system according to the present invention including: an imaging section that images an observed region; an image processing section that generates an observation image of the observed region from an imaging signal obtained by the imaging section; a display section that displays the generated observation image; a light source section that selectively switches a plurality of kinds of illumination light different in spectroscopic characteristics to apply the illumination light to the observed region; an illumination mode changing section that changes the kind of illumination light applied from the light source section; and a light source control section that controls, based on a light amount control signal, a light amount of the illumination light emitted from the light source section, wherein the light source control section multiplies a value of the light amount control signal indicating a ratio relative to a maximum value of a light amount in an illumination mode before changing by a light amount ratio preset between different illumination modes to set a value of the light amount control signal for illumination light in an illumination mode after changing.

According to the present invention, since fluctuation of the light amount of the illumination light caused by changing of the illumination mode is suppressed, brightness of the observation image is prevented from discontinuously changing in changing of the illumination mode. Moreover, control of the light amount of the illumination light after changing of the illumination mode converges quickly.

BRIEF DESCRIPTION OF THE DRAWINGS

FIG. 6A illustrates a white light observation image; FIG. 6B illustrates a special light observation image;

FIG. 13 is an explanatory drawing of another aspect of the light source device.

DETAILED DESCRIPTION OF THE PREFERRED EMBODIMENTS

Hereafter, embodiments for implementing the present invention is described in detail with reference to the accompanying drawings.

[Entire Configuration of Endoscope System]

Figure 1:
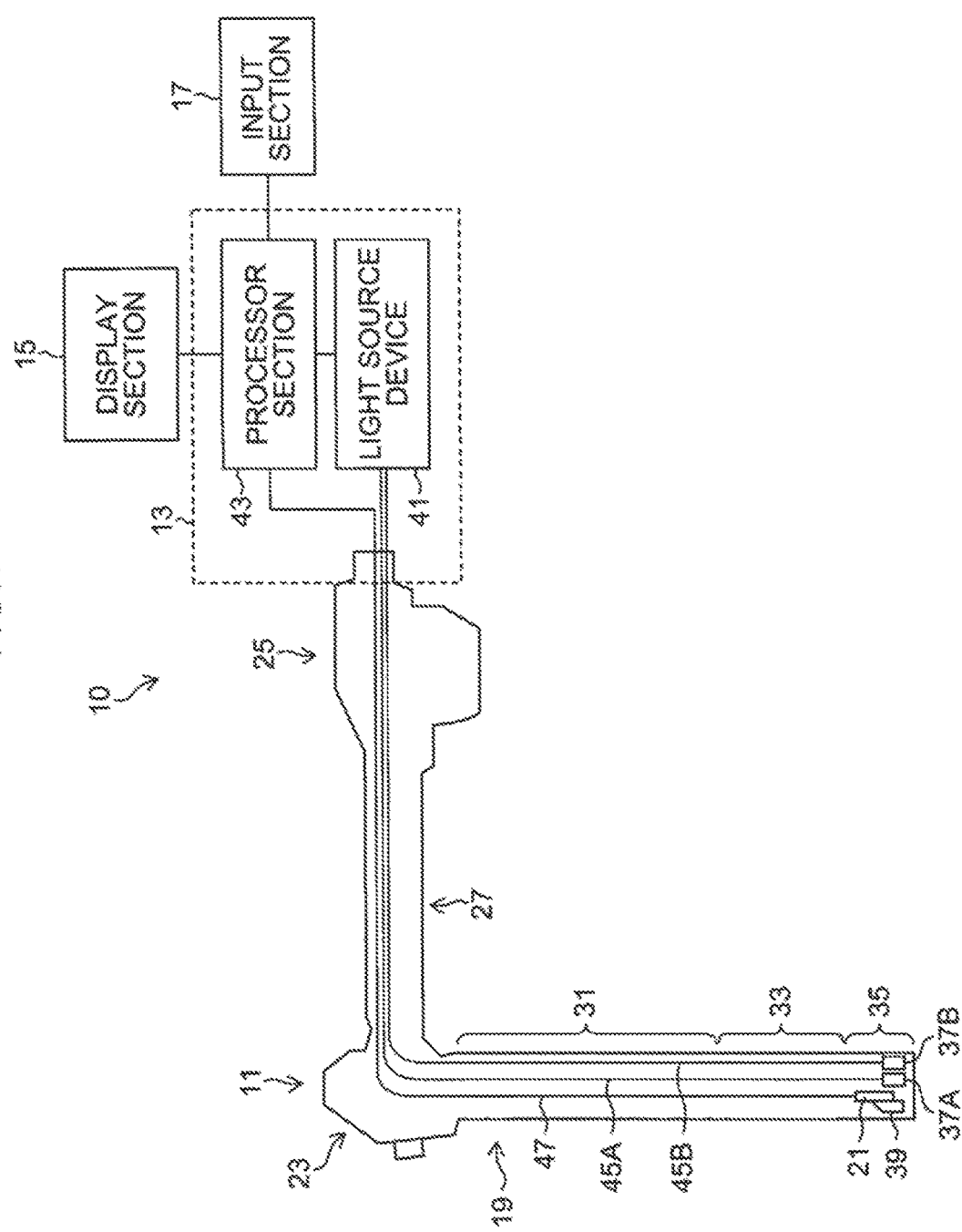
FIG. 1 is an entire configuration diagram of an endoscope system according to an embodiment of the present invention.

FIG. 1 is an entire configuration diagram of an endoscope system according to an embodiment of the present invention.

An endoscope system 10 illustrated in FIG. 1 is configured to include an endoscope body 11, a control apparatus 13 to which the endoscope body 11 is connected, a display section 15 and an input section 17.

The endoscope body 11 is an electronic endoscope including an illumination optical system emitting illumination light from a leading end of an endoscope insertion part 19 to be inserted into an object, and an imaging optical system including an imaging element imaging an observed region.

The endoscope body 11 includes an operation section 23 for bending operations of the leading end of the endoscope insertion part 19 and/or operations of suction, air supply/water supply and the like from the leading end of the endoscope insertion part 19, a connector section 25 that enables the endoscope body 11 to be detachably connected to the control apparatus 13, and a universal cord section 27 that joins the operation section 23 with the connector section 25.

In addition, not shown in the figure by omission, inside the endoscope body 11, various kinds of channels such as a forceps channel for inserting a treatment tool for collecting tissue and the like and an air supply/water supply channel are provided.

The endoscope insertion part 19 is configured of a flexible part 31 having flexibility, a bending part 33 to be bent according to bending operations and an endoscope leading end part 35. Note that the endoscope leading end part 35 is sometimes abbreviated as a "leading end part 35" in the following description.

In the endoscope leading end part 35, irradiation ports 37A and 37B through which light is applied to an observed region and an imaging element 21 obtaining image information of the observed region are disposed.

The imaging element 21 employs a CCD (Charge Coupled Device) image sensor or a CMOS (Complementary Metal-Oxide Semiconductor) image sensor. To the imaging element 21, an imaging member 39 such as an objective lens is attached.

The bending part 33 is provided between the flexible part 31 and leading end part 35 and is configured to be able to be freely bent according to wire operations from the operation section 23, actuation operations from an actuator, and the like. The bending part 33 can be bent in arbitrary directions and by arbitrary angles depending on portions of the object for which the endoscope body 11 is used, thereby enabling observation directions of the irradiation ports 37A and 37B and the imaging element 21 of the endoscope leading end part 35 to be directed toward desired observation portions.

In addition, not shown in the figure by omission, in the irradiation ports 37A and 37B of the endoscope insertion part 19, cover glasses and/or lenses are disposed.

Inside the endoscope body 11, optical fibers 45A and 45B for guiding illumination light from a light source device 41 and a scope cable 47 connecting the imaging element 21 to a processor section 43 are inserted therethrough.

Moreover, not shown in the figure by omission, various kinds of signal lines from the operation section 23 and various kinds of tubes such as air supply and water supply channels are also connected to the control apparatus 13 and the like through the universal cord section 27 and connector section 25.

The connector section 25 illustrated in FIG. 1 is detachably connected to the control apparatus 13. The optical fibers 45A and 45B are connected to the light source device 41 in the control apparatus 13 through the connector section 25, and the scope cable 47 is connected to the processor section 43 in the control apparatus 13 through the connector section 25.

Figure 2:
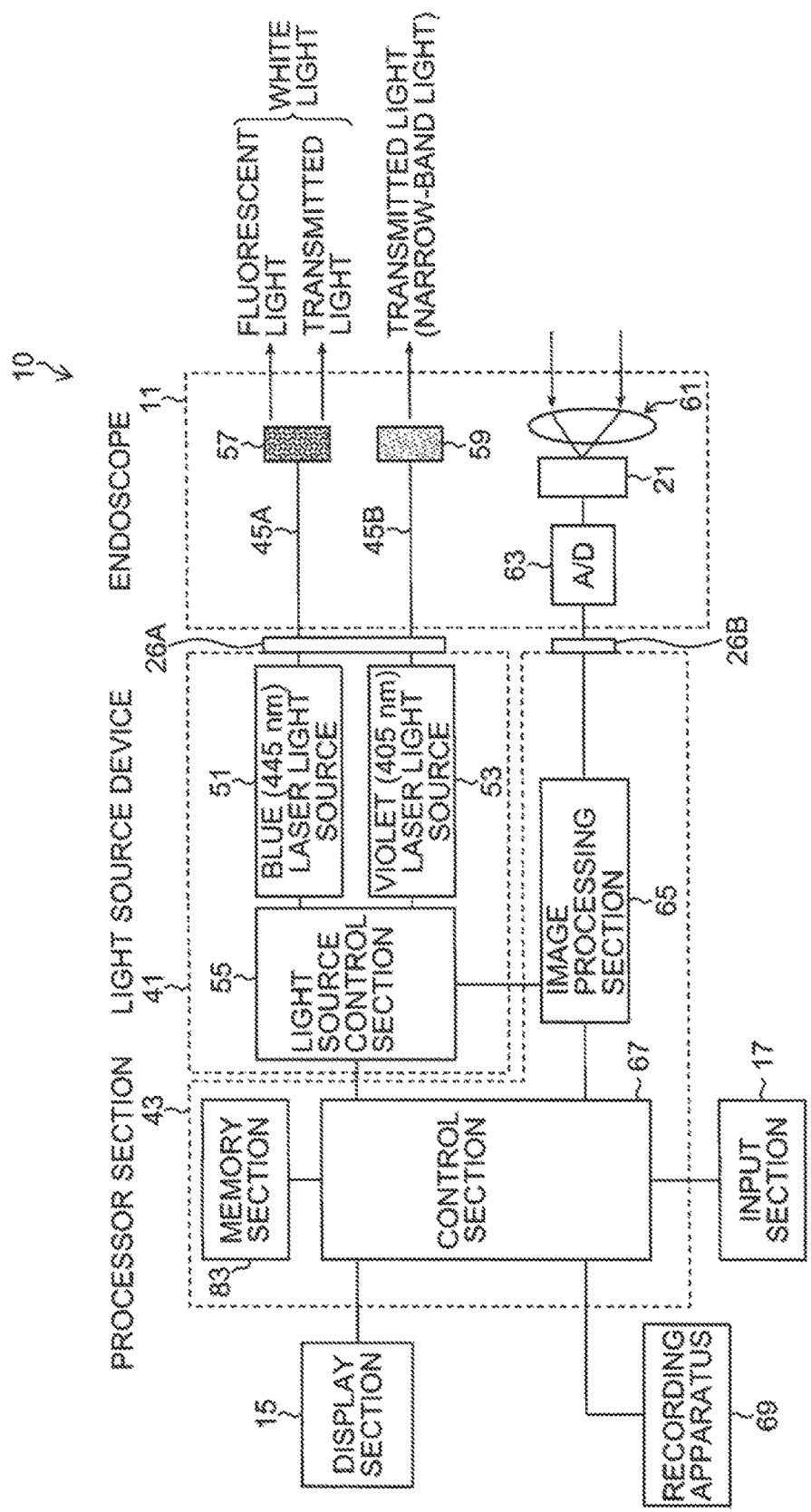
FIG. 2 is a block diagram of the endoscope system illustrated in FIG. 1.

The optical fibers 45A and 45B are connected to the light source device 41 by a connector section (not shown in FIG. 1; shown in FIG. 2, accompanied by reference character 26A). Moreover, the scope cable 47 is connected to the processor section 43 by a connector section (not shown in FIG. 1; shown in FIG. 2, accompanied by reference character 26B).

To the control apparatus 13 illustrated in FIG. 1, the display section 15 on which an observation image of the object, additional information of the observation image and the like are displayed and the input section 17 that accepts input operations performed by an operator are connected.

Moreover, the control apparatus 13 includes the light source device 41 generating illumination light supplied to the irradiation ports 37A and 37B of the endoscope leading end part 35, and the processor section 43 that performs image processing on image signals from the imaging element 21.

The processor section 43 performs image processing on imaging signals transmitted from the endoscope body 11, based on instructions from the operation section 23 of the endoscope body 11 or the input section 17, and generates an observation image to be displayed by the display section 15.

Operation commands (operation command signals) sent from the input section 17 are sent to the processor section 43, and command signals corresponding to the operation signals are sent to the individual portions of the apparatus from the processor section 43. Exemplary configurations of the input section 17 can include a keyboard, a mouse, a joystick and the like.

Moreover, the display section 15 may be a touch-panel display apparatus, and buttons, switches and the like displayed on the display section 15 may constitute the input section 17.

FIG. 2 is a block diagram of the endoscope system illustrated in FIG. 1. In the following description, elements same as or similar to those having been previously described are provided with the same reference characters and the description for those is omitted.

As illustrated in FIG. 2, the light source device 41 includes a blue laser light source 51 with a center wavelength of 445 nanometers and a violet laser light source 53 with a center wavelength of 405 nanometers as light-emitting sources. Light amounts from the blue laser light source 51 and violet laser light source 53 as semiconductor light-emitting elements (light amounts) are individually controlled by a light source control section 55.

Namely, based on command signals sent from the control section 67, light amounts of the blue laser light source 51 and violet laser light source 53 are individually controlled by the light source control section 55, and thereby, a light amount of illumination light applied from the leading end part 35 of the endoscope body 11 is controlled (mentioned later in detail).

The blue laser light source 51 and violet laser light source 53 can employ InGaN-based laser diodes of a broad area type. Moreover, an InGaNAs-based laser diode and/or a GaNAs-based laser diode can also be employed. Furthermore, for the blue laser light source 51 and violet laser light source 53, there may be a configuration in which light-emitting bodies such as light-emitting diodes are used.

Laser light emitted from the blue laser light source 51 and violet laser light source 53 is introduced into optical fibers (not shown) through collector lenses which are not shown, and transmitted to the endoscope leading end part 35 (see, FIG. 1) of the endoscope body 11 by the optical fibers 45A and 45B, respectively, through a connector section 26A and the connector section 25 on the endoscope body 11 side.

Then, the laser light emitted from the blue laser light source 51 is applied to a fluorescent material 57 as a wavelength conversion member disposed in the endoscope leading end part 35, and the laser light emitted from the violet laser light source 53 is applied to a light polarization/diffusion member 59.

The not-shown optical fibers in the light source device 41 and the optical fibers 45A and 45B in the endoscope body 11 are multimode fibers, and as one example, thin cables each of which has a core diameter of 105 micrometers and a cladding diameter of 125 micrometers and whose diameter including a protective layer as an outer cover is $\phi$0.3 millimeters to $\phi$0.5 millimeters can be used.

The fluorescent material 57 is configured to include a plurality of kinds of fluorescent materials which absorb part of blue laser light from the blue laser light source 51 and induce excited-light emission of green to yellow (for example, YAG-based (Yttrium Aluminum Garnet-based) fluorescent materials, fluorescent materials containing BAM ($BaMgAl10O17$) and the like, or the like).

Thereby, combination of excited light of green to yellow due to excitation light which is the blue laser light from the blue laser light source 51 with the transmitted blue laser light that is not absorbed by the fluorescent material 57 affords white illumination light.

As the endoscope system 10 presented in the example, using a semiconductor light-emitting element as an excitation light source affords white light with high intensity in high light emission efficiency and the intensity of the white light can be easily adjusted. Furthermore, change in color temperature and chromaticity of the white light is small.

The light polarization/diffusion member 59 is configured of material transmitting laser light from the violet laser light source 53, and for example, employs a resin material having transparency, glass, or the like. Furthermore, configurations of providing fine roughness on the surface or the like of the resin material or glass and/or providing a light diffusion layer in which particles (filler or the like) with different refractive indices are mixed thereon, or configurations of using translucent materials may be employed.

Transmitted light emitted from the light polarization/diffusion member 59 is illumination light with a narrow-band wavelength (special light) whose light amount is uniform within a predetermined illumination region.

Including the fluorescent material 57 and light polarization/diffusion member 59 can prevent phenomena of convolution of noise which disrupts imaging, occurrence of flickering in displaying a moving image, and the like, these caused by speckles arising from coherence of laser light.

The fluorescent material 57 is preferable to be configured of material in which particle diameters of a fluorescent substance itself and a filler are set such that light in an infrared region is little absorbed and highly dispersed in consideration of a refractive index difference between the fluorescent substance constituting the fluorescent material and fixing and solidifying resin as the filler.

A configuration of including the fluorescent material 57 can enhance a dispersion effect without decreasing the light intensity of red-band and/or infrared-band light and to make means for changing a light path such as a concave lens unnecessary, this reducing optical loss.

Figure 3:
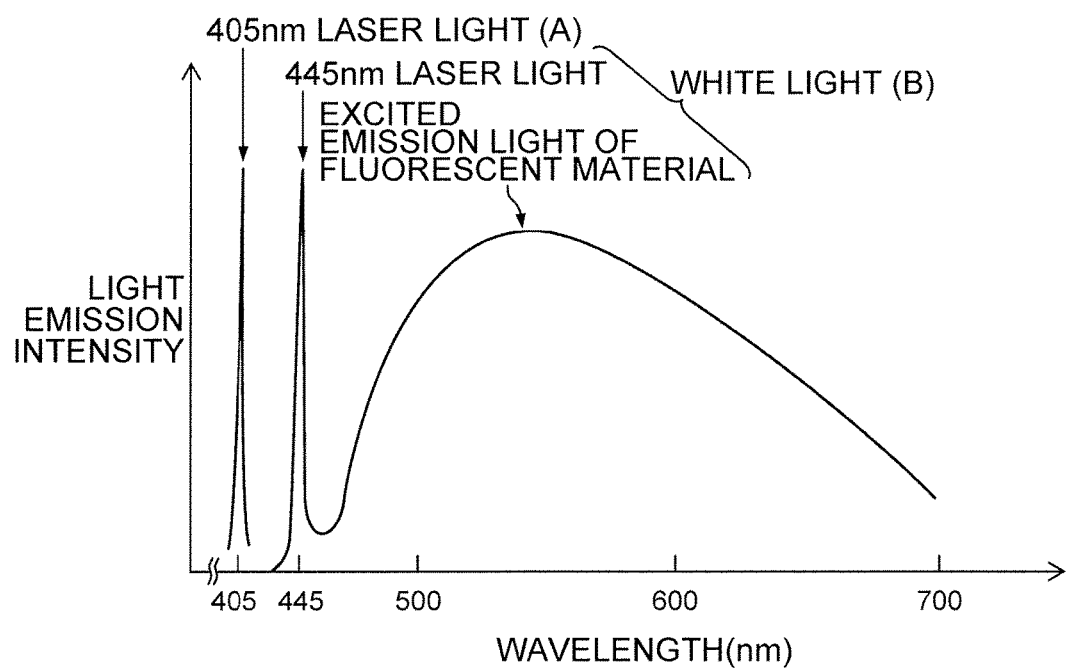
FIG. 3 is a graph illustrating emission spectra of laser light from a violet laser light source, and laser light from a blue laser light source and light after wavelength conversion on blue laser light with a fluorescent material.

FIG. 3 is a graph illustrating emission spectra of laser light from the violet laser light source 53, and blue laser light from the blue laser light source 51 and light after wavelength conversion on the blue laser light with the fluorescent material 57.

The violet laser light from the violet laser light source 53 is indicated by an emission line with a center wavelength of 405 nanometers (profile A). Moreover, the blue laser light from the blue laser light source 51 is indicated by an emission line with a center wavelength of 445 nanometers, and the excited emission light due to the blue laser light from the fluorescent material 57 presents a spectral intensity distribution in which the light amount increases in a wavelength band of 450 nanometers to 700 nanometers (profile B).

The center wavelength of 405 nanometers for the violet laser light and the center wavelength of 445 nanometers for the blue laser light are representative and not limiting.

Profile B constituted of the excited emission light and the blue laser light forms the white light. The "white light" in the present specification is not limited to the one strictly containing all the wavelength components in visible light, but for example, may be one containing light in specific wavelength bands such as R, G and B and may also include light containing wavelength components from green to red, light containing wavelength components from blue to green, or the like.

In other words, in the endoscope system 10, it is possible to relatively increase or decrease the light amounts of profile A and profile B to generate illumination light, and thereby, illumination light whose characteristics vary according to a mixing ratio of profiles A and B can be obtained.

Returning to FIG. 2, the illumination light formed by the blue laser light source 51, fluorescent material 57 and violet laser light source 53 is applied toward an observed region of the object from the leading end part 35 of the endoscope body 11.

Then, via an imaging lens 61, the observed region to which the illumination light is applied is imaged on the imaging element 21 to be imaged as the observed region (object).

An imaging signal obtained from the imaging element 21 by imaging the observed region is converted into a digital signal by an A/D converter 63 and sent to an image processing section 65 of the processor section 43.

In the image processing section 65, image processing is performed on the inputted image signal in a digital form, an observation image which can be displayed on the display section 15 is generated and displayed on the display section 15. Moreover, it is printed by a recording apparatus (printer) 69 as needed. The recording apparatus 69 may be built in the processor section 43, or may be connected to the processor section 43 via a network.

Not shown in FIG. 2 by omission, a memory apparatus such as a storage apparatus, a semiconductor memory medium and a magnetic memory medium may be included and the observation image may be stored therein as image data. Furthermore, associated with the observation image, additional information of the observation image may be stored along with the image data of the observation image.

In the additional information of the observation image, observation conditions such as an observation mode and an illumination mode (illumination conditions), imaging conditions of an imaging section (shown in FIG. 4, accompanied by reference character 114) which includes the imaging element 21, an image processing mode, and other additional conditions are included.

[Detailed Description of Image Processing Section]

Figure 4:
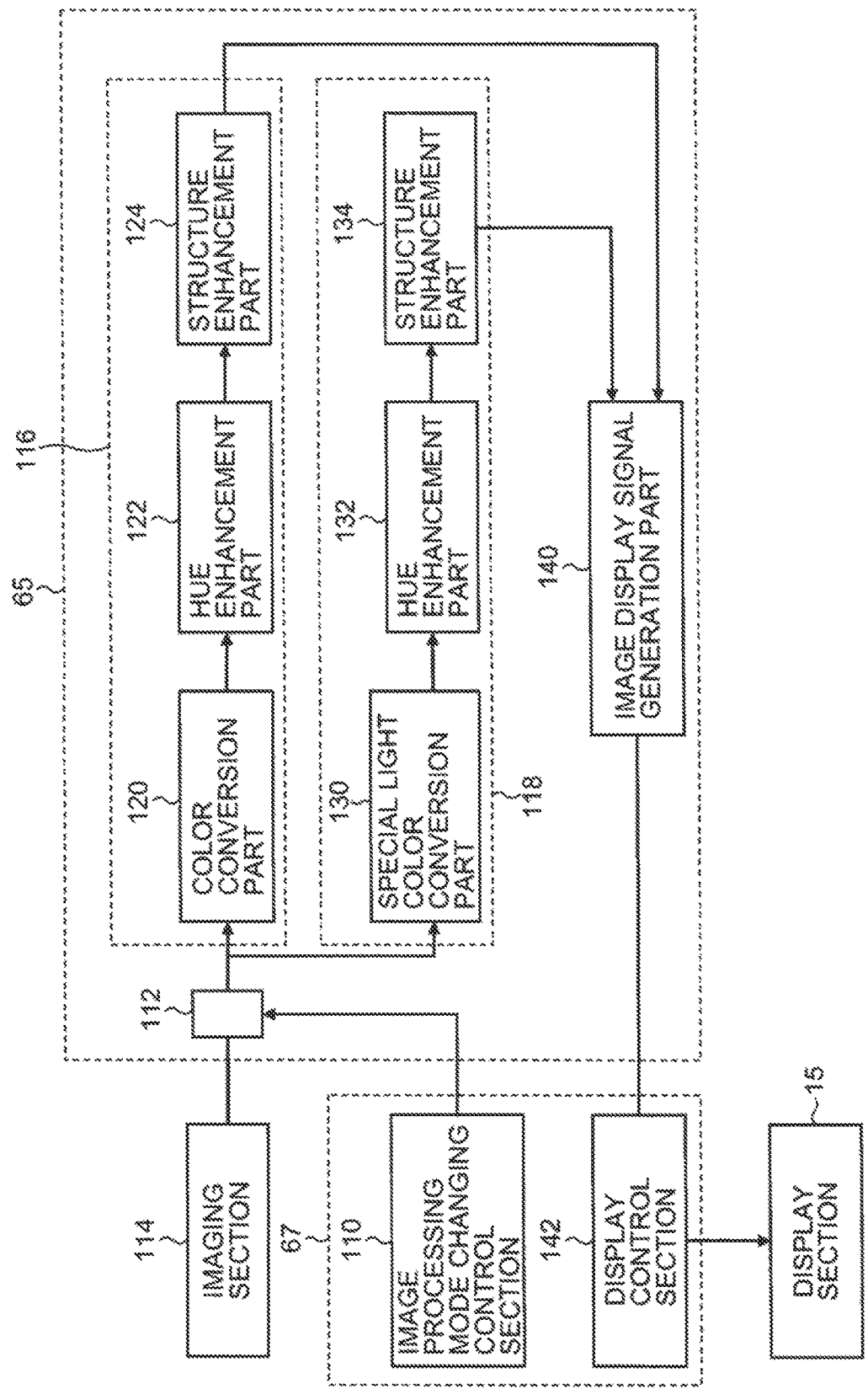
FIG. 4 is a block diagram illustrating an exemplary configuration of an image processing section illustrated in FIG. 2.

Next, the image processing section 65 illustrated in FIG. 2 is described in detail. FIG. 4 is a block diagram illustrating an exemplary configuration of the image processing section 65 and the periphery of the image processing section 65.

The image processing section 65 presented in the example can perform changing between white light image processing (normal observation image processing) corresponding to a white light observation mode (normal observation mode) of using white light as illumination light and special light image processing corresponding to a special light observation mode of using special light.

Namely, upon changing of an observation mode by an observer's operation, a control signal is sent from an image processing mode changing control section 110 of the control section 67 to an image processing mode changing section 112 of the image processing section 65.

The image processing mode changing section 112 performs switching of an imaging signal obtained by an imaging section 114 to be sent to a white light image processing section 116 that performs the white light image processing or to be sent to a special light image processing section 118 that performs the special light image processing.

Herein, the imaging section 114 illustrated in FIG. 4 includes the imaging lens 61 (optical system) and imaging element 21 illustrated in FIG. 2, and in addition, includes a CDS circuit (not shown) performing correlated double sampling (CDS) on the imaging signal, an AGC circuit (not shown) performing automatic gain control (AGC), and the A/D converter 63 (see, FIG. 2) converting the analog signal having undergone the sampling and gain control into a digital signal.

The white light image processing section 116 illustrated in FIG. 4 includes a color conversion part 120, a hue enhancement part 122 and a structure enhancement part 124, and performs processing on the imaging signal obtained in the white light observation mode and converted in a digital form.

The color conversion part 120 performs gradation conversion processing and color conversion processing on a digital imaging signal for each of R, G and B to generate image data for each color of R, G and B. For example, in the image data for each color of R, G and B, with reference to a color conversion table, a gradation value is converted into a concentration value for each color of R, G and B.

The hue enhancement part 122 performs hue enhancement processing of discriminating blood vessels from mucosa in the image regarding their shades to enhance the blood vessels so as to be seen easily, with respect to the image data for each color of R, G and B. Examples of the hue enhancement processing can include processing of enhancing hue in a direction of discriminating blood vessels from mucosa regarding their shades over an average shade of the entire image in consideration of the average shade of the entire image (frame).

The structure enhancement part 124 performs structure enhancement processing such as sharpness and edge enhancement on the image data for each color of R, G and B which data has undergone the hue enhancement processing. The image data for each color of R, G and B which data has undergone the structure enhancement processing performed by the structure enhancement part 124 is sent to an image display signal generation part 140.

The special light image processing section 118 includes a special light color conversion part 130, a hue enhancement part 132 and a structure enhancement part 134, and performs processing on the imaging signal obtained in the special light observation mode.

In the special light observation mode, red (R) narrow-band light suitable for observation of a middle layer and a deep layer of body tissue is not used, but blue (B) narrow-band light suitable for observation of superficial layer tissue and green (G) narrow-band light suitable for observation of middle layer tissue and superficial layer tissue are used.

Namely, a G image signal (G narrow-band data) is multiplied by a predetermined coefficient and allocated to R image data, and a B image signal (B narrow-band data) is multiplied by a predetermined coefficient and allocated to G image data, and in addition, is multiplied by a predetermined coefficient and allocated to B image data, these generating a pseudo-color image constituted of the three channel-color image data.

Since the pseudo-color image thus generated contains much B image data mainly containing information of superficial layer tissue, it presents status of superficial layer tissue, micro blood vessels and/or microstructure more in detail, this enabling the micro blood vessels and/or microstructure of the superficial layer tissue to be observed easily.

The special light color conversion part 130 performs gradation conversion processing and color conversion processing. After that, a G image signal is multiplied by a coefficient and allocated to R image data, and a B image signal is multiplied by a coefficient and allocated to G image data and B image data, these generating image data for each color of R, G and B.

The hue enhancement part 132 performs processing of enhancement in a direction of discriminating blood vessels from mucosa in the image (frame) regarding their shades to enhance the blood vessels so as to be seen easily with respect to the image data for each color of R, G and B which data is generated by the special light color conversion part 130.

The structure enhancement part 134 performs structure enhancement processing such as sharpness and edge enhancement on the image data for each color of R, G and B after the hue enhancement processing.

In the structure enhancement part 134, the image data for each color of R, G and B which data has undergone the structure enhancement processing is sent to the image display signal generation part 140 as image data for each color of R, G and B which data has undergone the special light image processing.

The image display signal generation part 140 converts the image data for each color of R, G and B generated by the processing in the parts of the white light image processing section 116 or the image data for each color of R, G and B generated by the processing in the parts of the special light image processing section 118 into an observation image data which can be displayed by the display section 15.

The observation image data for display converted by the image display signal generation part 140 is sent to the display section 15 through the display control section 142 and displayed on the display section 15.

[Description of Object Observation]

Next, an example of using the above-mentioned endoscope system 10 for observation of a blood vessel image of a body tissue superficial layer is described.

Figure 5:
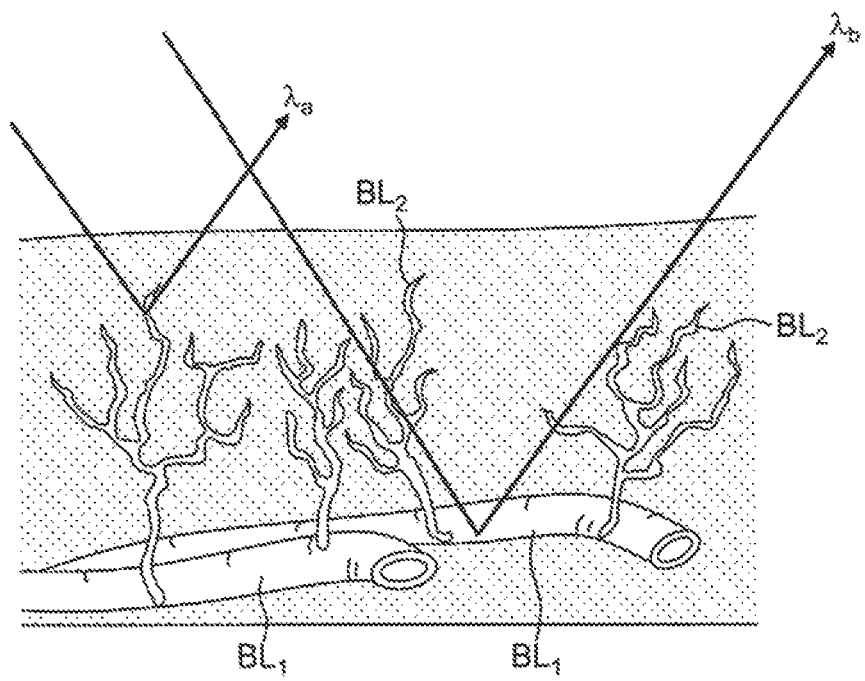
FIG. 5 is an explanatory drawing schematically illustrating blood vessels in a mucosal surface of body tissue.

FIG. 5 is an explanatory drawing schematically illustrating blood vessels in a mucosal surface of body tissue. The mucosal surface of body tissue is reported in which capillary blood vessels $BL_2$ such as a dendritic vascular network are formed to extend from a blood vessel $BL_1$ in deep mucosa to the mucosal surface, lesions of body tissue being exhibited in microstructure of the capillary blood vessels $BL_2$ and the like.

Accordingly, attempts have been being made in recent years to find a micro lesion in early stage or to diagnose a range of lesions by performing image enhancement on, and thus, observing capillary vessels in a mucosal surface with specific narrow wavelength-band light using an endoscope system.

When illumination light is incident into body tissue, the incident light diffusively propagates in the body tissue. The absorption/dispersion characteristics of body tissue have wavelength dependency and the dispersion characteristics tend to be stronger as the wavelength is shorter.

In other words, a degree of light reaching a deep position changes according to an illumination light wavelength, while blood flowing in blood vessels has a local maximum of absorption in wavelengths of approximately 400 nanometers to 420 nanometers, this allowing large contrast.

For example, when the illumination light is in a wavelength band $\lambda_a$ with a wavelength of approximately 400 nanometers, blood vessel information is obtained from capillary vessels in a mucosal surface, and when it is in a wavelength band $\lambda_b$ with a wavelength of approximately 500 nanometers, blood vessel information including blood vessels in a deeper layer is obtained.

Due to this, when blood vessels in a body tissue superficial layer is observed, a light source is used with a center wavelength not less than 360 nanometers and not more than 800 nanometers, preferably not less than 365 nanometers and not more than 515 nanometers, and further preferably, a center wavelength not less than 400 nanometers and not more than 470 nanometers.

Figure 6A:
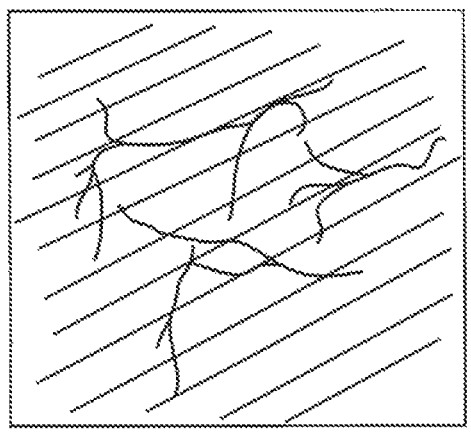
FIGS. 6A and 6B are explanatory drawings of schematic display examples of observation images obtained by the endoscope system.
Figure 6B:
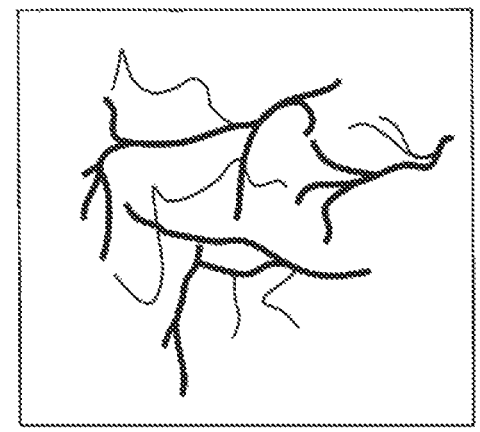

FIGS. 6A and 6B are explanatory drawings of schematic display examples of observation images obtained by an endoscope system. FIG. 6A represents an observation image in a white light observation mode and FIG. 6B represents an observation image in a special light observation mode.

As illustrated in FIG. 6A, for the observation image in the white light observation mode in which illumination light is white light (pseudo-white light), while a blood vessel image of relatively deep mucosa is obtained, fine capillary vessels in a mucosal surface is seen blurry. On the other hand, for the observation image, illustrated in FIG. 6B, in the special light observation mode in which the illumination light is special light formed in a narrow band of only short wavelengths, the fine capillary vessels in the mucosal surface is seen clear.

In the endoscope system 10 presented in the example, a mixing ratio between blue laser light with a center wavelength of approximately 445 nanometers (for example, 445 nanometers±10 nanometers) from the blue laser light source 51 and violet laser light with a center wavelength of approximately 405 nanometers (for example, 405 nanometers±10 nanometers) from the violet laser light source 53 can be adjusted by the light source control section 55 (see, FIG. 2).

Examples of adjusting the mixing ratio between blue laser light and violet laser light can include an aspect of manipulating a switch 89 provided in the operation section 23 of the endoscope body 11 illustrated in FIG. 1 to perform image enhancement such that capillary vessels in a mucosal surface can be observed more easily.

In other words, as to illumination light applied to the observed object, when the mixing ratio of blue laser light is made relatively large, while clearness of the fine capillary vessels in the mucosal surface decreases, shortage of the illumination light amount is not liable to arise. For example, the observation image illustrated in FIG. 6A is obtained.

On the other hand, when the mixing ratio of violet laser light is made relatively large, the fine capillary vessels, as illustrated in FIG. 6B, relatively close to the mucosal surface is observed clearly. Meanwhile, shortage of the illumination light amount is liable to arise, the shortage of the light amount arising in observation in a distant view and the observation image being dark. Thus, by adjusting the mixing ratio between blue laser light and violet laser light, a balance between the clearness of the fine capillary vessels in the mucosal surface and brightness of the observation image in observation in a distant view is adjusted.

In the endoscope system 10 presented in the example, both of the blood vessel information obtained using blue laser light and the blood vessel information closer to the superficial layer obtained using violet laser light can be extracted and displaying them on the display section 15 (see, FIG. 1) enables the observer to compare both with each other.

Therefore, the blood vessel information containing the blood vessels closer to the superficial layer which cannot be observed using blue laser light can be observed in high visibility.

[Description of Observation Mode Changing]

Next, the observation mode changing of the endoscope system 10 presented in the example is described in detail.

First Embodiment

Figure 7:
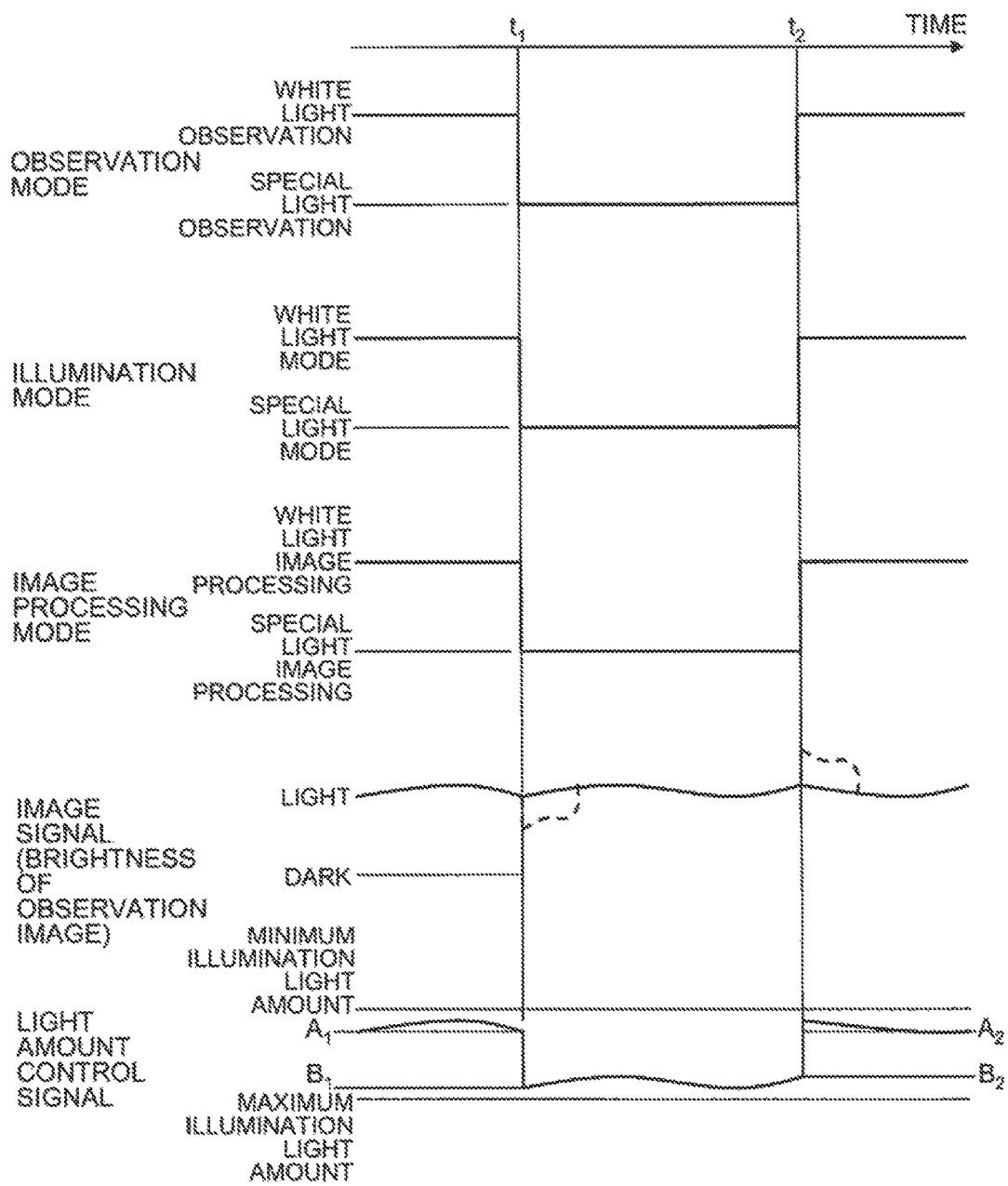
FIG. 7 is a block diagram illustrating an exemplary configuration of a control section and a light source control section according to a first embodiment.
Figure 8:
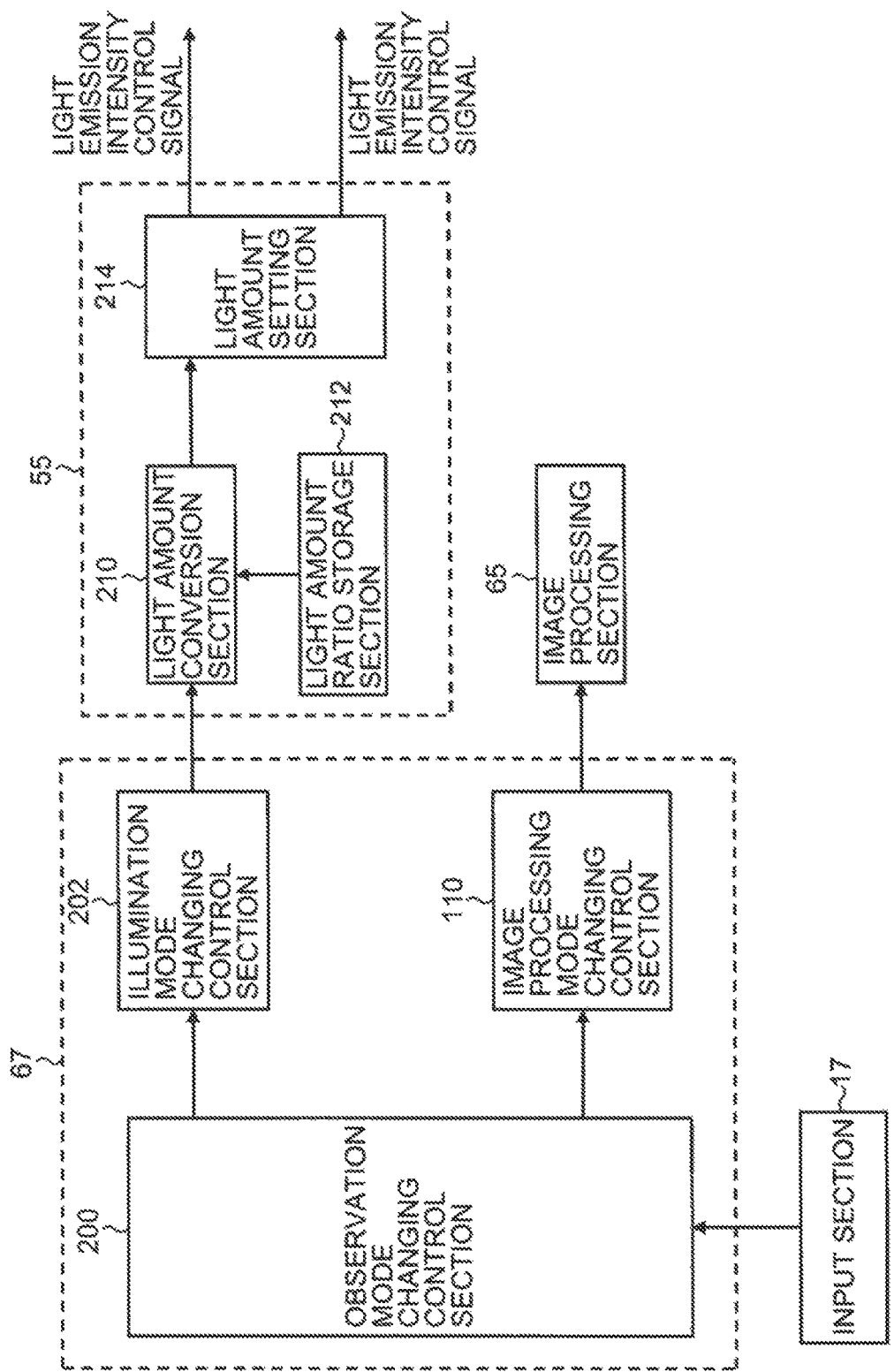
FIG. 8 is an explanatory drawing of switching of an observation mode according to the first embodiment.

FIG. 7 is an explanatory drawing of the observation mode changing according to a first embodiment. Moreover, FIG. 8 is a block diagram illustrating an exemplary configuration of the control section 67 and light source control section 55 according to the embodiment.

FIG. 7 illustrates relationship between a changing command of an observation mode, changing timing of an illumination mode, changing timing of an image processing mode, an image signal (change in brightness of an observation image), and a light amount control signal.

The light amount control signal illustrated in FIG. 7 represents a value in a control signal of the light amount of illumination light. Relationship between measurements of the light amount control signal represents relationship between measurements of the light amount of illumination light. In addition, the lateral series in FIG. 7 represents time and time elapses from left to right in the figure.

At timing $t_1$ in FIG. 7, when the observation mode is changed from the white light observation mode to the special light observation mode in synchronization with the timing of the changing command of the observation mode, the illumination mode is changed from the white light mode to the special light mode and the image processing mode is changed from the white light image processing to the special light image processing.

Moreover, a value $A_1$ of the light amount control signal of the illumination light used in the white light observation mode immediately before the changing timing $t_1$ of the observation mode is stored. Based on the stored value $A_1$ of the light amount control signal of the illumination light before changing, a value $B_1$ of the light amount control signal of the illumination light used in the special light observation mode after changing of the observation mode is calculated.

The value $A_1$ of the light amount control signal of the illumination light used in the white light observation mode and the value $B_1$ of the light amount control signal of the illumination light used in the special light observation mode satisfy:

$$B_1 = A_1 \times k_1$$

($k_1$ is a constant exceeding 1).

The constant $k_1$ mentioned above is presented by:

$k_1$=(standard value of the light amount of the illumination light in the special light observation mode)/(standard value of the light amount of the illumination light in the normal observation mode), beforehand calculated and held (stored) inside.

At the changing timing $t_1$ of the observation mode, since the value $A_1$ of the light amount control signal of the illumination light used in the white light observation mode is changed to the value $B_1$ of the light amount control signal of the illumination light used in the special light observation mode (>$A_1$), the image signal (observation image) is prevented from being relatively dark at the changing timing $t_1$ of the observation mode.

Similarly, at timing $t_2$, when the observation mode is changed from the special light observation mode to the white light observation mode in synchronization with changing of the observation mode, the illumination mode is changed from the special light mode to the white light mode and the image processing mode is changed from the special light image processing to the white light image processing.

A value $B_2$ of the light amount control signal of the illumination light used in the special light observation mode before the changing timing $t_2$ of the observation mode is stored. Based on the stored value $B_2$ of the light amount control signal of the illumination light before changing of the observation mode, a value $A_2$ of the light amount control signal of the illumination light used in the white light observation mode after the changing timing $t_2$ of the observation mode is calculated ($A_2 = B_2 \times k_2$ ($k_2$ is a constant less than 1)).

In addition, the constant $k_1$ may be associated with the constant $k_2$, satisfying:

$$k_1 = 1/k_2 \text{ or}$$

the constant $k_1$ and constant $k_2$ may be coefficients independent from each other.

At the changing timing $t_2$ of the observation mode, since the value $B_2$ of the light amount control signal of the illumination light used in the special light observation mode is changed to the value $A_2$ of the light amount control signal of the illumination light used in the white light observation mode, the image signal (observation image) is prevented from being relatively light at the changing timing $t_2$ of the observation mode.

The broken lines illustrated for the image signal in FIG. 7 indicate that brightness of the image signal changes when the value of the light amount control signal of the illumination light is not changed before and after changing of the observation mode.

Such adjustment of the light amount of the illumination light upon the observation mode changing illustrated in FIG. 7 is realized by a configuration illustrated in FIG. 8. FIG. 8 illustrates an exemplary configuration for realizing adjustment of the light amount of the illumination light upon the changing of the observation mode illustrated in FIG. 7.

As illustrated in FIG. 8, the control section 67 (see, FIG. 2) includes the image processing mode changing control section 110 (see, FIG. 2) and further includes an observation mode changing control section 200 and an illumination mode changing control section 202.

For example, upon changing operation of the observation mode in the input section 17, an observation mode changing command signal is sent to the observation mode changing control section 200. After that, based on the command signal, a changing command signal of the image processing mode is sent to the image processing mode changing control section 110 and a changing command signal of the illumination mode is sent to the illumination mode changing control section 202, from the observation mode changing control section 200.

According to the illumination mode changing command signal, a changing signal of the illumination mode is sent from the illumination mode changing control section 202 to the light source control section 55. Moreover, according to the image processing mode changing command signal, a command signal of the image processing mode is sent from the image processing mode changing control section 110 to the image processing section 65.

The light source control section 55 (see, FIG. 2) is configured to include a light amount conversion section 210, a light amount ratio storage section 212 and a light amount setting section 214.

The light amount conversion section 210 calculates a setting value of the light amount of the illumination light immediately after changing of the observation mode (for example, $B_1$ in FIG. 7) from a setting value of the light amount of the illumination light immediately before changing of the observation mode (for example, $A_1$ in FIG. 7), and sends the setting value of the light amount of the illumination light immediately after changing of the observation mode to the light amount setting section 214.

The light amount ratio storage section 212 stores light amount ratios between the observation modes (illumination modes) (for example, the constants $k_1$ and $k_2$ mentioned above).

The light amount conversion section 210 refers to the light amount ratio stored in the light amount ratio storage section 212, and calculates the value of the light amount control signal of the illumination light used in the illumination mode after changing of the observation mode. The calculated value of the light amount control signal is sent to the light amount setting section 214, and based on the value of the light amount control signal, the light amounts of the blue laser light source 51 and violet laser light source 53 illustrated in FIG. 2 are set.

For the light source device 41 (see, FIG. 2) presented in the example, in case of any of the white light mode and special light mode, the value of the light amount control signal is set to a ratio (0 percent to 100 percent) relative to the maximum value.

For example, in case where the value of the light amount control signal of the illumination light used in the white light observation mode is 70 percent, the value of the light amount control signal of the illumination light used in the special light observation mode after changing of the observation mode is set to a value exceeding 70 percent.

On the other hand, in case where the value of the light amount control signal of the illumination light used in the special light observation mode is 70 percent, the value of the light amount control signal of the illumination light used in the white light observation mode after changing of the observation mode is set to a value less than 70 percent.

This light amount control of the light source device 41 is only one example and the present invention can be applied to any other than the aspect of setting based on the ratio of the light amount control signal relative to the maximum value.

According to the endoscope system configured as mentioned above, upon change from the white light observation mode to the special light observation mode, the value of the light amount control signal of the illumination light used in the illumination mode after changing of the observation mode is determined in consideration of difference in light amount of the illumination light used in the illumination mode after changing of the observation mode. Therefore, brightness of the observation image (screen) does not change discontinuously before and after changing the observation mode.

Moreover, compared with a case where change in brightness of the observation image based on changing of the observation mode is not considered, the light amount control signal after changing of the observation mode converges quickly.

Second Embodiment

Figure 9:
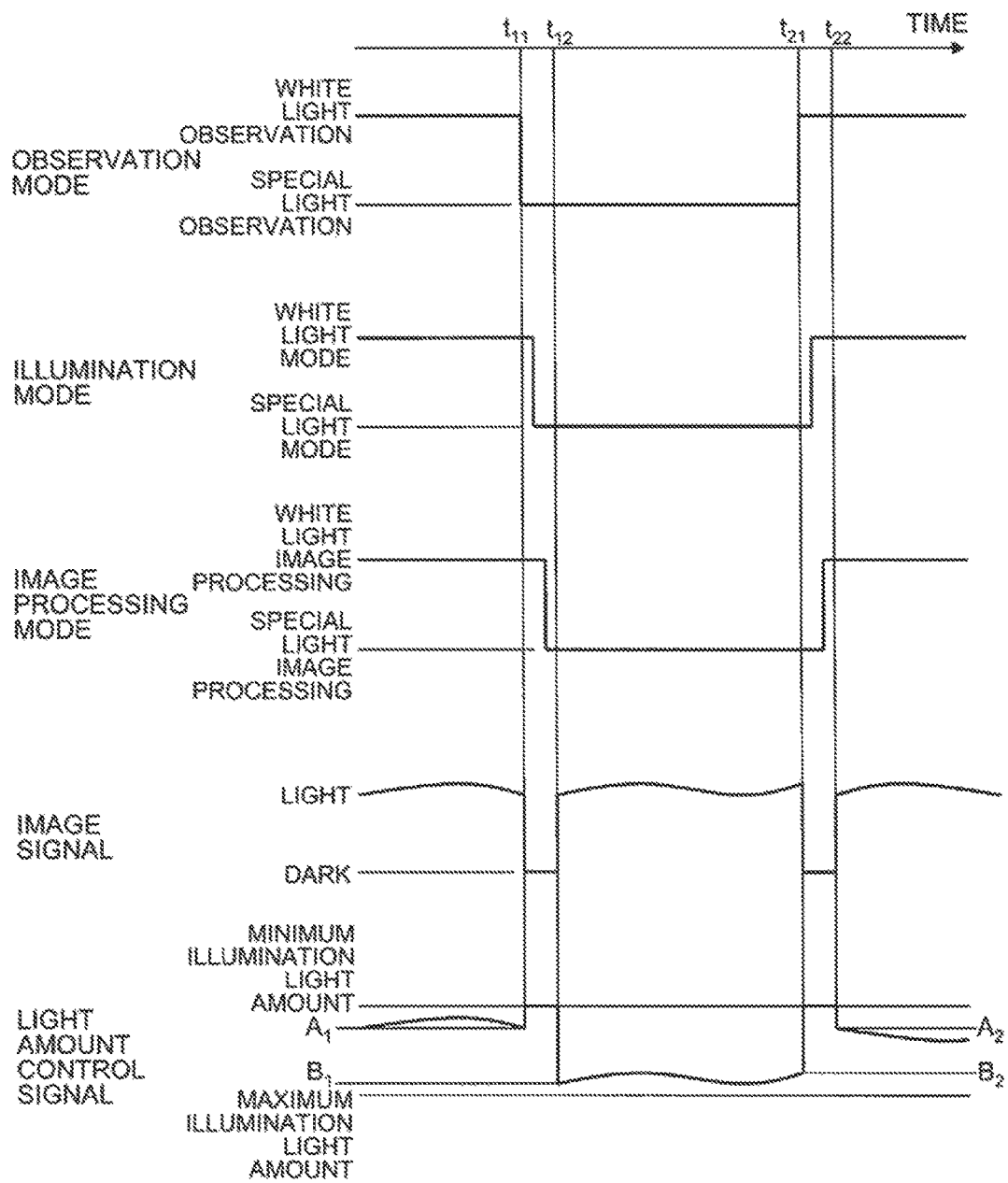
FIG. 9 is an explanatory drawing of switching of the observation mode according to a second embodiment.
Figure 10:
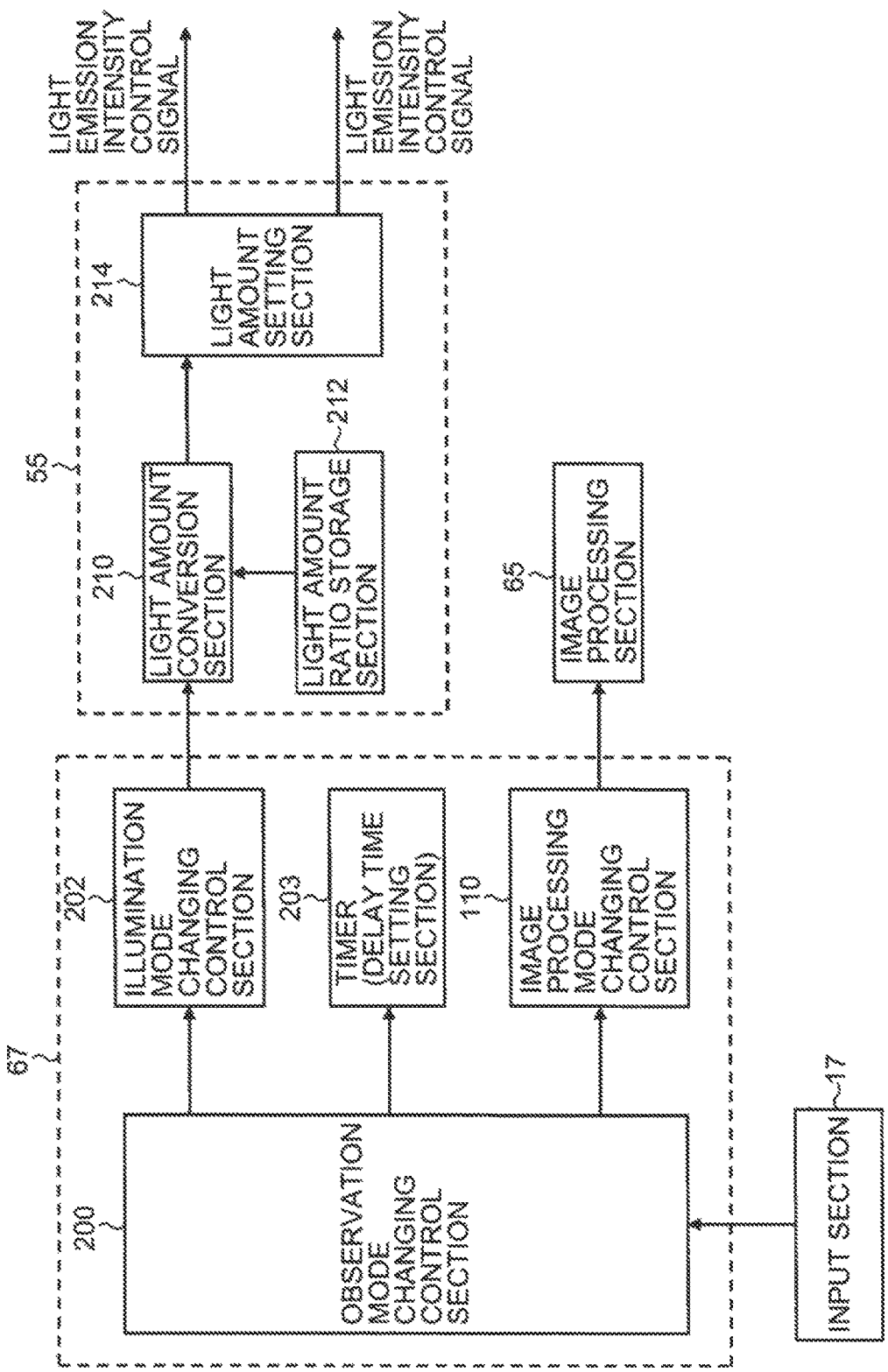
FIG. 10 is a block diagram illustrating an exemplary configuration of the control section and the light source control section according to the second embodiment.

Next, the observation mode changing according to a second embodiment is described. FIG. 9 is an explanatory drawing of the observation mode changing according to the second embodiment, and FIG. 10 is a block diagram illustrating an exemplary configuration of the control section 67 and light source control section 55 according to the embodiment.

In the observation mode changing according to the second embodiment, changing of the observation mode, changing of the illumination mode and changing of the image processing mode are performed asynchronously. Within a period from timing $t_{11}$ to timing $t_{12}$ during which period the observation mode is changed from the white light observation to the special light observation, the illumination mode is changed from the white light mode to the special light mode and the image processing mode is changed from the white light image processing to the special light image processing.

Moreover, during the period from the timing $t_{11}$ to the timing $t_{12}$ during which period the observation mode is changed from the white light observation to the special light observation, the value of the light amount control signal of the illumination light used in the special light mode is set as a preset fixed value (for example, the minimum value within the setting range).

The "minimum value" noted herein may be zero as the light amount control signal (no light emission) or a minimum value which is not zero and is determined from observation conditions.

At the timing $t_{12}$ when changing of the illumination mode and image processing mode completes, the value of the light amount control signal is changed from the minimum value to $B_1$.

Even when changing of the observation mode is asynchronous with changing of the illumination mode and image processing mode, brightness of the observation image is suppressed from irregularly fluctuating toward the bright side after changing of the observation mode.

Similarly, within a period from timing $t_{21}$ to $t_{22}$ during which period the observation mode is changed from the special light observation to the white light observation, the illumination mode is changed from the special light mode to the white light mode and the image processing mode is changed from the special light image processing to the white light image processing.

During the period from the timing $t_{21}$ to the timing $t_{22}$, the light amount of the illumination light is set to the minimum value, and at the timing $t_{22}$, the value of the light amount control signal of the illumination light used in the white light observation mode is changed from the minimum value to $A_2$.

Also when the special light observation mode is changed to the white light observation mode, brightness of the observation image is suppressed from fluctuating toward the bright side after changing of the observation mode.

In the block diagram illustrated in FIG. 10, compared with the configuration illustrated in FIG. 8, a timer (delay time setting section) 203 that determines delay time from the changing timing of the observation mode is added. The timer 203 determines a period until the light amount of the light source device 41 is set to the minimum value from the changing timing of the observation mode (period from $t_{11}$ to $t_{12}$; period from $t_{21}$ to $t_{22}$).

The delay time determined by the timer 203 may be adjusted according to the light amount setting value before changing or set to a fixed value. The delay time can be not more than 10 cycles of a changing interval of the observation image (not more than 10 frames in frame number of the observation image).

Figure 11A:
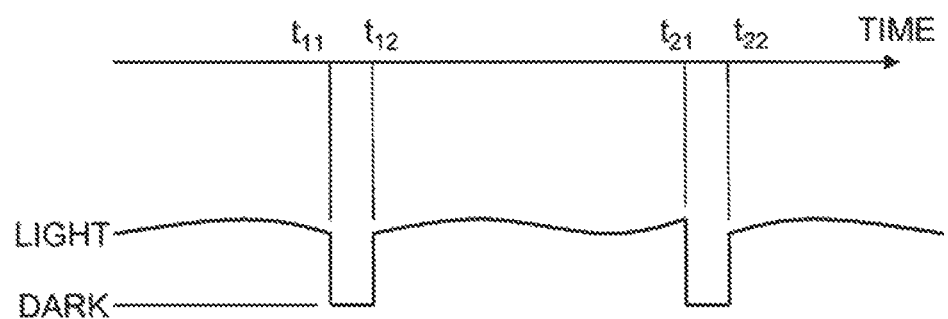
FIGS. 11A and 11B are explanatory drawings of an effect of observation mode switching according to the second embodiment.
Figure 11B:
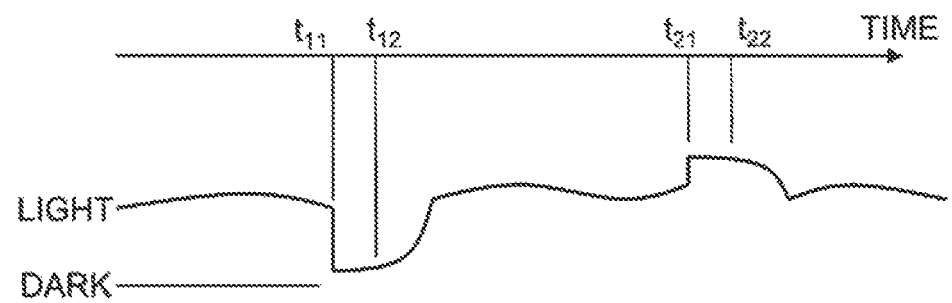

FIGS. 11A and 11B are explanatory drawings of an effect of the observation mode changing according to the second embodiment. FIG. 11A schematically illustrates an image signal (brightness of the observation image) in the observation mode changing according to the second embodiment.

Meanwhile, FIG. 11B schematically illustrates an image signal (brightness of the observation image) in case of no adjustment of the light amount of the illumination light in changing of the observation mode. As illustrated in the figure, in the case of no adjustment of the light amount of the illumination light in changing of the observation mode, brightness of the observation image fluctuates in changing of the observation mode.

On the contrary, as illustrated in FIG. 11A, in the case of adjustment of the light amount of the illumination light in changing of the observation mode, although the observation image becomes dark because the light amount of the illumination light is set to the minimum value, brightness of the observation image is suppressed from fluctuation that the observer can visually recognize compared with fluctuation of the observation image being bright, and the light amount of the illumination light after changing of the observation mode converges quickly.

In the example, upon changing of the observation mode, the light amount of the illumination light is set to the minimum value for a certain period, whereas the observation image immediately before the changing timing of the observation mode may be displayed for the relevant certain period.

Moreover, timing of changing of the illumination mode and timing of changing of the image processing mode may be determined arbitrarily. The image processing mode may be changed after changing of the illumination mode, or the illumination mode may be changed after changing of the image processing mode. The illumination mode and the image processing mode may be changed simultaneously.

[Variations of Light Source Device]

Next, endoscope systems in which the configuration of the light source device 41 (see, FIG. 2) is changed are described.

Figure 12:
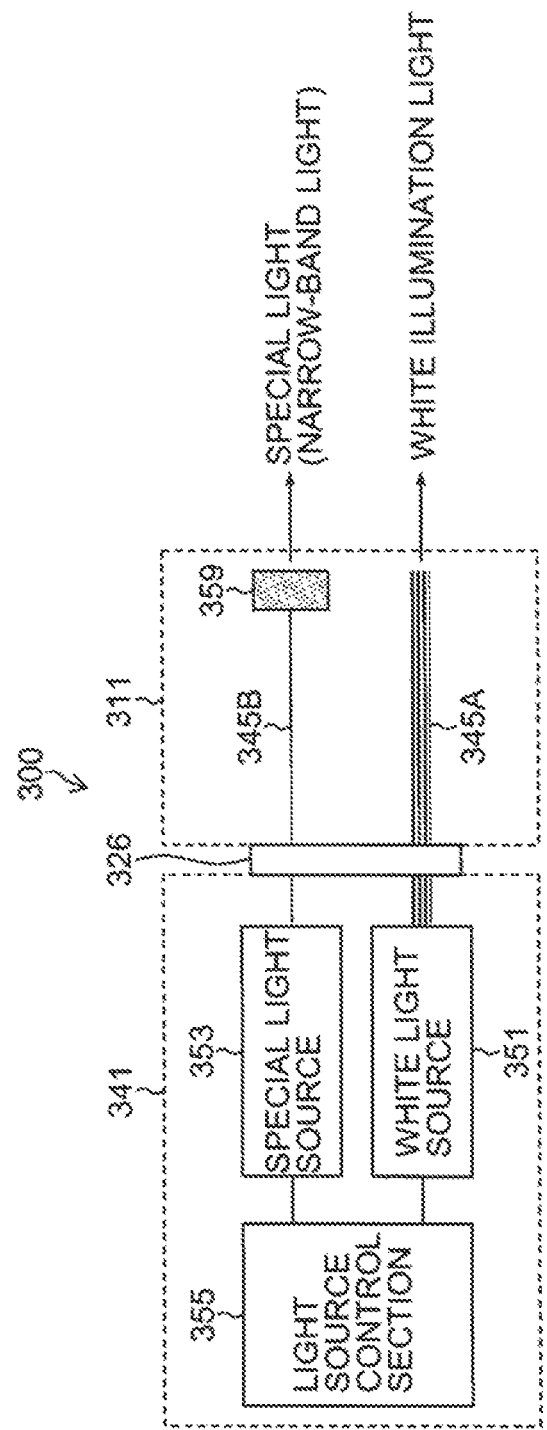
FIG. 12 is an explanatory drawing of another aspect of a light source device.

FIG. 12 is a block diagram of a schematic configuration of an endoscope system 300 including a light source device 341. In the figure, part of the configuration such as the processor section 43 (see, FIG. 2) is omitted from illustration.

The light source device 341 of the endoscope system 300 illustrated in FIG. 12 employs a light source that emits broad (corresponding to broad-band) wavelength-band light such as a halogen lamp, a xenon lamp and a white light-emitting diode as a white light source 351.

White light emitted from the white light source 351 is applied toward the observed region from the leading end part (shown in FIG. 1, accompanied by reference character 35) of an endoscope 311 through a light guide 345A as an optical fiber bundle.

Moreover, a special light source 353 illustrated in FIG. 12 employs the violet laser light source 53 illustrated in FIG. 1. Special light emitted from the special light source 353 is sent to the leading end part of the endoscope 311 through a connector section 326 and an optical fiber 345B.

Furthermore, it is applied as narrow-band light toward the observed region through a light polarization/diffusion member 359 disposed at the light emission end of the optical fiber 345B. In addition, the light polarization/diffusion member 359 may be replaced by a light emission window disposed in the leading end part of the endoscope body 11.

According to the endoscope system 300 illustrated in FIG. 12, white light that has broad spectroscopic characteristics corresponding to broad band and has a high color rendering property can be realized by a simple configuration, and in addition, heat generation of the endoscope leading end part is suppressed.

Moreover, white light and special light (narrow-band light) can be applied completely separately and narrow-band light is emitted onto the observed region not through the fluorescent material (shown in FIG. 2, accompanied by reference numeral 57). Therefore, undesired light emission from the fluorescent material can be prevented and light amount control can be performed easily.

FIG. 13 is a block diagram of an endoscope system 400 according to an aspect of a changed configuration of the special light source 353 in FIG. 12. In the figure, elements same as or similar to those in FIG. 12 are provided with the same reference characters and the description of those is omitted. Moreover, in FIG. 13, an optical system for white light is omitted.

From the endoscope system 400 illustrated in the figure, a special light source that emits special light is omitted and narrow-band light (special light) is generated using the white light source 351 and optical filters 402 (402A, 402B and 402C).

Light applied from the white light source 351 and transmitted through the optical filters 402 is guided to the light incident end of a light guide 454 through a condenser member 404 and guided to the leading end part of an endoscope 411 by the light guide 454.

Each of the optical filters 402A, 402B and 402C is a narrow band-pass filter transmitting only predetermined narrow-band wavelength components in the incident white light and each of those corresponds to a different band from one another.

The optical filters 402A, 402B and 402C are formed in part of a rotation filter plate 405 and any of the optical filters 402A, 402B and 402C can be selectively changed by driving and rotating the rotation filter plate 405 by means of a drive mechanism 406 including a motor and the like.

In other words, the optical filters 402A, 402B and 402C which are two or more kinds are selectively switched and disposed in the middle of the light path of the white light, and thereby, special light corresponding to a plurality of kinds of narrow bands different from one another can be emitted.

According to the endoscope system 400 illustrated in FIG. 13, special light (narrow-band light) corresponding to arbitrary wavelength bands can be generated from the white light source.

Moreover, an aspect of the optical filters 402A, 402B and 402C illustrated in FIG. 13 being filters corresponding to R, G and B or another aspect of providing a filter corresponding to special light can be applied.

As above, the endoscope system presented in the example can employ a frame sequential imaging method using a light source device switching R, G and B sequentially for each frame or a light source device switching normal light and special light sequentially for each frame.

In such a frame sequential imaging method, upon switching of the kind of illumination light (illumination mode) for each frame, the illumination light is switched automatically in place of the changing command of the observation mode illustrated in FIG. 7 and FIG. 9.

Moreover, the image processing mode may be switched in synchronization with switching of the illumination light or only has to be switched within preset delay time from the switching timing of the illumination light.

As above, the endoscope system according to the embodiments of the present invention is described, whereas the present invention is not limited to the above-mentioned embodiments but modifications, additions and eliminations of components thereof may occur within the spirit and scope of the present invention.

[Invention Disclosed in Present Specification]

As comprehended from the above-mentioned description of the embodiments according to the present invention, the present specification includes disclosure of various technical ideas at least including the following aspects.

(First aspect): An endoscope system including: an imaging section that images an observed region; an image processing section that generates an observation image of the observed region from an imaging signal obtained by the imaging section; a display section that displays the generated observation image; a light source section that selectively switches a plurality of kinds of illumination light different in spectroscopic characteristics to apply the illumination light to the observed region; an illumination mode changing section that changes the kind of illumination light applied from the light source section; and a light source control section that controls, based on a light amount control signal, a light amount of the illumination light emitted from the light source section, wherein the light source control section multiplies a value of the light amount control signal indicating a ratio relative to a maximum value of a light amount in an illumination mode before changing by a light amount ratio preset between different illumination modes to set a value of the light amount control signal for illumination light in an illumination mode after changing.

According to the aspect, since fluctuation of the light amount of the illumination light caused by changing of the illumination mode is suppressed, brightness of the observation image is prevented from discontinuously changing in changing of the illumination mode. Moreover, control of the light amount of the illumination light after changing of the illumination mode converges quickly.

(Second aspect): The endoscope system according to the first aspect, further including an observation mode changing section that instructs changing of an observation mode including at least changing of the illumination mode by the illumination mode changing section, wherein the illumination mode changing section changes the illumination mode in synchronization with an observation mode changing instruction or after the observation mode changing instruction when the observation mode changing instruction is given by the observation mode changing section.

According to the aspect, since fluctuation of the light amount of the illumination light caused by changing of the illumination mode due to changing of the observation mode is suppressed in changing of the observation mode, brightness of the observation image is prevented from discontinuously changing in changing of the observation mode. Moreover, control of the light amount of the illumination light after changing of the observation mode converges quickly.

(Third aspect): The endoscope system according to the second aspect, wherein the illumination mode changing section changes the illumination mode in synchronization with the observation mode changing instruction when the observation mode changing instruction is given by the observation mode changing section.

According to the aspect, since the illumination mode is changed in synchronization with the changing instruction of the observation mode, brightness of the observation image is suppressed from being unstable before and after the observation mode changing.

(Fourth aspect): The endoscope system according to the second aspect or the third aspect, further including an image processing mode changing section that changes an image processing mode in the image processing section in synchronization with the observation mode changing instruction when the observation mode changing instruction is given by the observation mode changing section.

According to the aspect, the observation image can be obtained corresponding to the illumination mode after changing of the observation mode.

(Fifth aspect): The endoscope system according to the second aspect, wherein the illumination mode changing section changes the illumination mode after the observation mode changing instruction when the observation mode changing instruction is given by the observation mode changing section, and the light source control section sets the value of the light amount control signal in the illumination mode after observation mode changing for a certain period after the observation mode changing instruction by the observation mode changing section to a preset fixed value, and changes the fixed value to the value of the light amount control signal in the illumination mode after the observation mode changing, after elapse of the certain period after the observation mode changing instruction.

According to the aspect, since the light amount of the illumination light is the fixed value during the period preset based on the changing instruction of the observation mode in the aspect of the illumination mode changed asynchronously with changing of the observation mode, brightness of the observation image is suppressed from discontinuously fluctuating caused by changing of the observation mode.

(Sixth aspect): The endoscope system according to the fifth aspect, further including an image processing mode changing section that changes an image processing mode in the image processing section in accordance with the illumination mode of the light source section, wherein the observation mode changing section instructs changing of the observation mode including changing of the image processing mode by the image processing mode changing section.

According to the aspect, the observation image can be obtained corresponding to the illumination mode after changing of the observation mode.

(Seventh aspect): The endoscope system according to the fifth aspect or the sixth aspect, wherein the light source control section sets the fixed value to a minimum value within a setting range of the light amount control signal in each illumination mode.

According to the aspect, even when the illumination mode is changed asynchronously with changing of the observation mode, brightness of the observation image does not fluctuate toward the bright side and the observer does not suffer from large stress.

(Eighth aspect): The endoscope system according to any of the fifth aspect to the seventh aspect, further including a delay time setting section that sets, as the certain period, delay time after the observation mode changing instruction by the observation mode changing section.

According to the aspect, when changing of the observation mode is asynchronous with changing of the illumination mode, brightness of the observation image is suppressed from irregularly fluctuating by changing the illumination mode within the set delay time after changing of the observation mode.

(Ninth aspect): The endoscope system according to any of the first aspect to the eighth aspect, further including a light amount ratio storage section that stores a light amount ratio between different illumination modes.

According to the aspect, the light amount of the illumination light after changing of the illumination mode can be calculated easily.

(Tenth aspect): The endoscope system according to the ninth aspect, wherein the light amount ratio is a value obtained by dividing a standard value of the light amount of the illumination light in the observation mode after changing by a standard value of the light amount of the illumination light in the observation mode before changing.

According to the aspect, the aspect is preferable to calculate and store the light amount ratio for each observation mode.

(Eleventh aspect): The endoscope system according to any of the second aspect to the tenth aspect, wherein the light source section includes: a first light source that emits violet laser light with a center wavelength of 405 nanometers±10 nanometers; a second light source that emits blue laser light with a center wavelength of 445 nanometers±10 nanometers; and a fluorescent material inducing excited-light emission upon application of the blue laser light, and the light source control section sets, in a normal observation mode, light radiated from the fluorescent material upon light emission from the second light source, as the illumination light, and sets, in a special light observation mode, light emitted from the first light source upon light emission from the first light source, as the illumination light.

According to the aspect, the observation image corresponding to each illumination light can be obtained by configuring capable of switching the illumination light in the broad-band wavelength region and the illumination light in the narrow-band wavelength region.

What is claimed is:

1. An endoscope system comprising:
an imager configured to image an observed region;
an image processor configured to generate an observation image of the observed region from an imaging signal obtained by the imager;
a light source configured to selectively switch a kind of illumination light between a white light and a special light having a wavelength narrower than the white light, and apply the illumination light to the observed region;
an illumination mode change controller configured to change the kind of illumination light applied from the light source; and
a light source controller configured to control a light amount of the illumination light emitted from the light source,
wherein when the kind of illumination light is switched from the white light to the special light by the illumination mode change controller, the light source controller adjusts a light amount of the special light to be larger than a light amount of the white light, and suppresses a fluctuation in brightness between an observation image obtained when the white light is used and an observation image obtained when the special light is used, compared to a case where the light amount of the special light is not adjusted.

2. The endoscope system according to claim 1, further comprising an observation mode change controller that instructs changing of an observation mode including at least changing of the kind of illumination light by the illumination mode change controller,
wherein the illumination mode change controller changes the kind of illumination light in synchronization with an observation mode changing instruction or after the observation mode changing instruction when the observation mode changing instruction is given by the observation mode change controller.

3. The endoscope system according to claim 2, wherein the illumination mode change controller changes the kind of illumination light in synchronization with the observation mode changing instruction when the observation mode changing instruction is given by the observation mode change controller.

4. The endoscope system according to claim 2, further comprising an image processing mode change controller that changes an image processing mode in the image processor in synchronization with the observation mode changing instruction when the observation mode changing instruction is given by the observation mode change controller.

5. The endoscope system according to claim 2, wherein the illumination mode change controller changes the kind of illumination light after the observation mode changing instruction when the observation mode changing instruction is given by the observation mode change controller, and
the light source controller sets the light amount of the special light to a preset fixed value for a certain period after the observation mode changing instruction by the observation mode change controller, and adjusts the light amount of the special light after elapse of the certain period after the observation mode changing instruction.

6. The endoscope system according to claim 5, further comprising an image processing mode change controller that changes an image processing mode in the image processor in accordance with the kind of illumination light of the light source,
wherein the observation mode change controller instructs changing of the observation mode including changing of the image processing mode by the image processing mode change controller.

7. The endoscope system according to claim 5, wherein the light source controller sets the fixed value to a minimum value within a setting range of the light amount of the special light.

8. The endoscope system according to claim 5, further comprising a delay time setter that sets, as the certain period, delay time after the observation mode changing instruction by the observation mode change controller.

9. The endoscope system according to claim 1, wherein the kind of illumination light is changed according to a position of the observed region in a depth direction.

10. An endoscope system comprising:
an imager configured to image an observed region;
an image processor configured to generate an observation image of the observed region from an imaging signal obtained by the imager;
a light source configured to selectively switch a kind of illumination light between a white light and a special light having a wavelength narrower than the white light, and apply the illumination light to the observed region;
an illumination mode change controller configured to change the kind of illumination light applied from the light source; and
a light source controller configured to control a light amount of the illumination light emitted from the light source,
wherein when the kind of illumination light is switched from the special light to the white light by the illumination mode change controller, the light source controller adjusts a light amount of the white light to be smaller than a light amount of the special light, and suppresses a fluctuation in brightness between an observation image obtained when the special light is used and an observation image obtained when the white light is used, compared to a case where the light amount of the white light is not adjusted.

11. The endoscope system according to claim 10, further comprising an observation mode change controller that instructs changing of an observation mode including at least changing of the kind of illumination light by the illumination mode change controller,
wherein the illumination mode change controller changes the kind of illumination light in synchronization with an observation mode changing instruction or after the observation mode changing instruction when the observation mode changing instruction is given by the observation mode change controller.

12. The endoscope system according to claim 11, wherein the illumination mode change controller changes the kind of illumination light in synchronization with the observation mode changing instruction when the observation mode changing instruction is given by the observation mode change controller.

13. The endoscope system according to claim 11, further comprising an image processing mode change controller that changes an image processing mode in the image processor in synchronization with the observation mode changing instruction when the observation mode changing instruction is given by the observation mode change controller.

14. The endoscope system according to claim 11, wherein the illumination mode change controller changes the kind of illumination light after the observation mode changing instruction when the observation mode changing instruction is given by the observation mode change controller, and
the light source controller sets the light amount of the white light to a preset fixed value for a certain period after the observation mode changing instruction by the observation mode change controller, and adjusts the light amount of the white light after elapse of the certain period after the observation mode changing instruction.

15. The endoscope system according to claim 14, further comprising
an image processing mode change controller that changes an image processing mode in the image processor in accordance with the kind of illumination light of the light source,
wherein the observation mode change controller instructs changing of the observation mode including changing of the image processing mode by the image processing mode change controller.

16. The endoscope system according to claim 14, wherein the light source controller sets the fixed value to a minimum value within a setting range of the light amount of the white light.

17. The endoscope system according to claim 14, further comprising a delay time setter that sets, as the certain period, delay time after the observation mode changing instruction by the observation mode change controller.

18. The endoscope system according to claim 10, wherein the kind of illumination light is changed according to a position of the observed region in a depth direction.

19. An endoscope system comprising:
an imager configured to image an observed region;
an image processor configured to generate an observation image of the observed region from an imaging signal obtained by the imager;
a plurality of light sources configured to emit laser lights having wavelengths different from each other;
an illumination mode change controller configured to change a kind of illumination light to be used for illuminating the observed region; and
a light source controller configured to control a light amount of the illumination light to be emitted from the plurality of light sources,
wherein when the illumination light is switched from a white light to a special light having a wavelength narrower than the white light based on an illumination light changing instruction at a first timing, the light source controller:
generates the special light by changing a light amount ratio between the laser lights emitted from the plurality of light sources,
before emitting the special light, adjusts light amounts of the laser lights to set the special light having a light amount which is larger than a light amount of the white light at the first timing, and
emits the special light having the set light amount to illuminate the observed region, thereby suppressing a fluctuation in brightness between an observation image which has been obtained by the white light at the first timing and an observation image which is to be obtained by the special light having the set light amount, compared to a case where the observed image is illuminated with the special light having a light amount which is the same as the light amount of the white light at the first timing.

20. An endoscope system comprising:
an imager configured to image an observed region;
an image processor configured to generate an observation image of the observed region from an imaging signal obtained by the imager;

a plurality of light sources configured to emit laser lights having wavelengths different from each other;

an illumination mode change controller configured to change a kind of illumination light to be used for illuminating the observed region; and a light source controller configured to control a light amount of the illumination light to be emitted from the plurality of light sources, wherein when the illumination light is switched to a white light from a special light having a wavelength narrower than the white light based on an illumination light changing instruction at a first timing, the light source controller:

generates the white light by changing a light amount ratio between the laser lights emitted from the plurality of light sources, before emitting the white light, adjusts light amounts of the laser lights to set the white light having a light amount which is smaller than a light amount of the special light at the first timing, and emits the white light having the set light amount to illuminate the observed region, thereby suppressing a fluctuation in brightness between an observation image which has been obtained by the special light at the first timing and an observation image which is to be obtained by the white light having the set light amount, compared to a case where the observed image is illuminated with the white light having a light amount which is the same as the light amount of the special light at the first timing.

* * * * *